US010306472B2

(12) United States Patent
Battiwalla et al.

(10) Patent No.: US 10,306,472 B2
(45) Date of Patent: May 28, 2019

(54) SECURE AUTHORIZATION IN AN IMPLANTABLE MEDICAL DEVICE SYSTEM

(71) Applicant: Cochlear Limited, Macquarie University, NSW (AU)

(72) Inventors: Xerxes Battiwalla, Denistone West (AU); Victor Rodrigues, Frenchs Forest (AU); Mark Aufflick, Petersham (AU); Ben Leslie, Enmore (AU)

(73) Assignee: Cochlear Limited, Macquarie University (AU)

( * ) Notice: Subject to any disclaimer, the term of this patent is extended or adjusted under 35 U.S.C. 154(b) by 208 days.

(21) Appl. No.: 15/158,128

(22) Filed: May 18, 2016

(65) Prior Publication Data
US 2017/0223540 A1 Aug. 3, 2017

Related U.S. Application Data

(60) Provisional application No. 62/288,053, filed on Jan. 28, 2016.

(51) Int. Cl.
*H04W 12/08* (2009.01)
*H04W 12/06* (2009.01)
*H04L 29/06* (2006.01)
*H04W 12/04* (2009.01)
(Continued)

(52) U.S. Cl.
CPC ............ *H04W 12/08* (2013.01); *G06F 19/00* (2013.01); *G16H 40/67* (2018.01); *H04L 63/0435* (2013.01); *H04L 63/0492* (2013.01); *H04L 63/0876* (2013.01); *H04W 12/04* (2013.01); *H04W 12/06* (2013.01); *H04L 2209/88* (2013.01)

(58) Field of Classification Search
CPC ..... H04W 12/08; H04W 12/04; H04W 12/06; H04L 63/0435; H04L 63/0442; H04L 63/0492; H04L 63/0876; H04L 9/30
USPC .......................................... 713/168-172, 182
See application file for complete search history.

(56) References Cited

U.S. PATENT DOCUMENTS 7,475,245 B1 * 1/2009 Healy ................. A61N 1/37252
607/57
7,831,828 B2 * 11/2010 Von Arx .............. A61B 5/0031
713/168
7,890,180 B2 2/2011 Quiles
(Continued)

OTHER PUBLICATIONS

Meng Zhang e tal, Towards Trustworthy Medical Devices and Body Area Networks, ACM, 2013.*
(Continued)

*Primary Examiner* — Shanto Abedin
(74) *Attorney, Agent, or Firm* — Edell, Shapiro & Finnan, LLC

(57) ABSTRACT

Embodiments presented herein are generally directed to techniques for enabling a user of a mobile electronic device to wirelessly control one or more functions of an implantable medical device system. The techniques presented herein establish a secure (encrypted) communication channel between the implantable medical device system and a central system associated with the manufacturer of the implantable medical device system and use the secure communication channel to authorize a user to wirelessly control one or more functions of the implantable medical device system via the mobile electronic device.

19 Claims, 5 Drawing Sheets

(51) Int. Cl.
*G06F 19/00* (2018.01)
*G16H 40/67* (2018.01)

(56) References Cited

U.S. PATENT DOCUMENTS

| | | | |
|---|---|---|---|
| 8,002,700 B2 | 8/2011 | Ferek-Petric et al. | |
| 8,494,647 B2 | 7/2013 | Quiles | |
| 2005/0204134 A1* | 9/2005 | Von Arx | A61N 1/37252 |
| | | | 713/168 |
| 2006/0030904 A1* | 2/2006 | Quiles | A61N 1/37252 |
| | | | 607/60 |
| 2007/0083246 A1* | 4/2007 | Mazar | A61N 1/37235 |
| | | | 607/60 |
| 2008/0034216 A1 | 2/2008 | Law | |
| 2008/0097908 A1* | 4/2008 | Dicks | A61B 5/0022 |
| | | | 705/50 |
| 2008/0097917 A1* | 4/2008 | Dicks | G06F 19/00 |
| | | | 705/51 |
| 2010/0016924 A1* | 1/2010 | Doerr | G16H 40/20 |
| | | | 607/60 |
| 2010/0228977 A1* | 9/2010 | Sievert | A61N 1/37282 |
| | | | 713/168 |
| 2011/0145588 A1* | 6/2011 | Stubbs | G16H 40/40 |
| | | | 713/182 |
| 2012/0215285 A1 | 8/2012 | Tahmasian et al. | |
| 2013/0096648 A1* | 4/2013 | Benson | A61N 1/37252 |
| | | | 607/60 |
| 2013/0108046 A1* | 5/2013 | Andersen | H04W 12/04 |
| | | | 380/270 |
| 2014/0185805 A1* | 7/2014 | Andersen | H04W 12/02 |
| | | | 380/270 |
| 2014/0188193 A1 | 7/2014 | Vamos et al. | |
| 2014/0317394 A1 | 10/2014 | Buhler et al. | |
| 2015/0011970 A1 | 1/2015 | Kamen et al. | |
| 2015/0032633 A1* | 1/2015 | Haider | G06Q 50/22 |
| | | | 705/51 |
| 2015/0089590 A1* | 3/2015 | Krishnan | H04L 63/08 |
| | | | 726/3 |
| 2015/0207626 A1* | 7/2015 | Neftel | G08C 17/02 |
| | | | 713/168 |

OTHER PUBLICATIONS

Inshil Doha et. al, Distributed authentication mechanism for secure channel establishment in ubiquitous medical sensor networks, IOS Press (Year: 2011).*

International Search Report and Written Opinion in counterpart International Application No. PCT/IB2017/050286, dated Apr. 24, 2017, 9 pages.

* cited by examiner

ESTABLISHING, VIA AN INTERMEDIARY MOBILE ELECTRONIC DEVICE, AN INDIRECT SECURE COMMUNICATION CHANNEL BETWEEN AN IMPLANTABLE MEDICAL DEVICE SYSTEM AND A CENTRAL SYSTEM — 302

USING THE INDIRECT SECURE COMMUNICATION CHANNEL TO AUTHORIZE A USER TO WIRELESSLY CONTROL ONE OR MORE FUNCTIONS OF THE IMPLANTABLE MEDICAL DEVICE SYSTEM VIA AN EXTERNAL DEVICE — 304

SECURE AUTHORIZATION IN AN IMPLANTABLE MEDICAL DEVICE SYSTEM

CROSS REFERENCE TO RELATED APPLICATIONS

This application claims priority to U.S. Provisional Application No. 62/288,053 entitled "Secure Authorization in an Implantable Medical Device System," filed Jan. 28, 2016, the content of which is hereby incorporated by reference herein.

BACKGROUND

Field of the Invention

The present invention relates generally to wireless communications in implantable medical device systems.

Related Art

Implantable medical device systems, which include one or more implantable components, provide a wide range of therapeutic benefits to recipients. The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

SUMMARY

In one aspect, a method is provided. The method comprises establishing, via an intermediary mobile device, an indirect secure communication channel between an implantable medical device system and a central system associated with a manufacturer of the implantable medical device system; and using the indirect secure communication channel to authorize a user to wirelessly control one or more functions of the implantable medical device system via an external device.

BRIEF DESCRIPTION OF THE DRAWINGS

Embodiments of the present invention are described herein in conjunction with the accompanying drawings, in which:

FIG. 5 is a flowchart of a method in accordance with embodiments presented herein.

DETAILED DESCRIPTION

Figure 1:
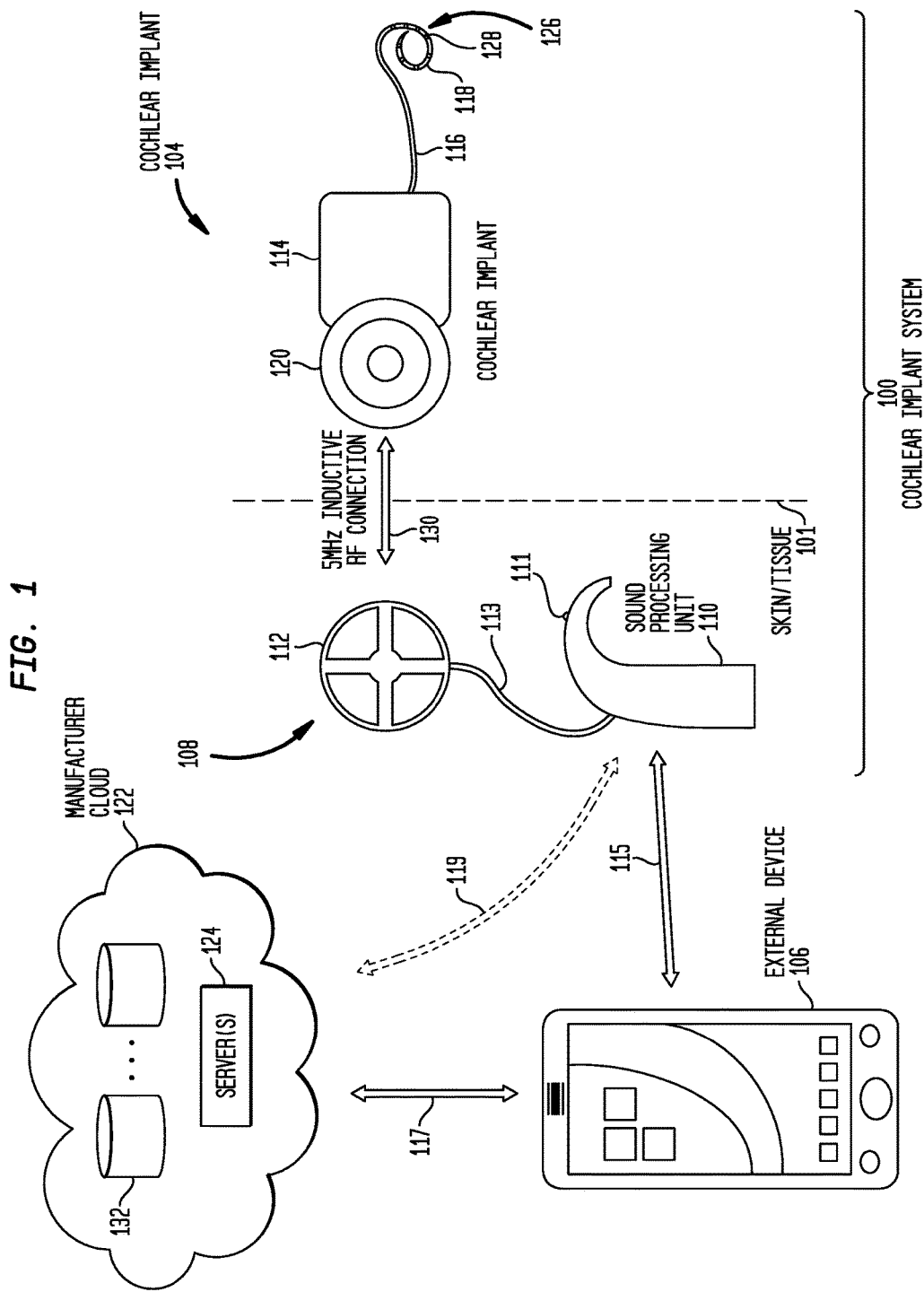
FIG. 1 is a schematic diagram illustrating a cochlear implant system in accordance with embodiments presented herein.

The use of smartphones, remote controls, and other mobile electronic devices is widespread and such devices are increasingly become integral to the daily routines of many individuals. As such, it may be desirable to enable a recipient of an implantable medical device system, such as a recipient of a cochlear implant system, to wirelessly control settings of the implantable medical device system using a smartphone, remote control, or other mobile electronic device (e.g., using a standard wireless communication protocol). In order to permit control over the implantable medical device system, a short-range wireless connection between the control entity and the system should be secured. However, conventional short-range wireless communication protocols, such as Bluetooth®, Bluetooth® Low Energy (LE) (BLE), etc., use encryption mechanisms that can be compromised, thus exposing all communication between a controller and the implantable medical device system to a potentially malicious third party and, potentially, allowing the third party to gain control over the implantable medical device system. Bluetooth® is a registered trademark owned by the Bluetooth® SIG.

As such, presented herein are techniques for enabling a user (e.g., the recipient, caregiver, clinician, surgeon, etc.) of a mobile electronic device to use the mobile electronic device to control one or more parameters, settings, operations, etc. (collectively and generally referred to herein as "functions") of an implantable medical device system. As described further below, the techniques presented herein establish/create a secure (encrypted) communication channel between the implantable medical device system and a central system associated with the manufacturer of the implantable medical device system and use the secure communication channel to authorize a user to wirelessly control one or more functions of the implantable medical device system via an external device.

The secure communication channel between the implantable medical device system and the central system is referred to herein as an "indirect" secure communication channel because the encrypted communications are relayed between the implantable medical device system and the central system via an intermediary mobile electronic device. That is, there is no direct connection between the implantable medical device system and the central system because the implantable medical device system lacks the ability to access a telecommunication network or a computing network (i.e., the implantable medical device system does not include a telecommunications interface or a network interface). As a result, a first portion of the indirect secure channel (i.e., a portion between the intermediary mobile electronic device and the implantable medical device system) overlays (runs on top of) a short-range wireless channel, while a second portion of the indirect secure channel (i.e., a portion between the intermediary mobile electronic device and the central system) overlays one or more telecommunication network links and/or computing network links (e.g., local area networks (LANs), wide area networks (WANs), etc.), collectively and generally referred to herein as network links. The indirect secure channel is additional to any encryption mechanisms already in use on the short-range wireless channel and/or the network links.

As described below, the techniques presented herein utilize a two-phase process/sequence to enable a mobile electronic device to control functions of an implantable medical device system. The first phase, referred to herein as the encryption phase, is used to establish the indirect secure channel between the implantable medical device system and the central system. The second phase, referred to herein as the authorization phase, uses the indirect secure channel to authorize a user to control one or more functions of the implantable medical device system via a mobile electronic device.

There are many types of implantable medical device systems that include one or more implantable components. However, merely for ease of illustration, the techniques presented herein are primarily described herein with reference to one type of implantable medical device system, namely a cochlear implant system. It is to be appreciated that the techniques presented herein may be used with other implantable medical device systems that include, for example, other partially and totally implantable hearing prostheses such as auditory brainstem stimulators, bone conduction devices, hybrid devices, implantable acoustic devices such as middle ear implants and direct acoustical cochlear stimulators, and/or other implantable medical devices such as implantable pacemakers, defibrillators, functional electrical stimulators, pain relief stimulators, visual prostheses, implantable sensors, and/or other systems having functional implantable components configured to diagnosis, prevent, monitor, treat or manage a disease or injury or symptom thereof, or configured to investigate, replace or modify the anatomy or of a physiological process.

FIG. 1 is a schematic diagram of an exemplary cochlear implant system 100 configured to implement aspects of the present invention. As shown, the cochlear implant system 100 includes an external component 108 configured to be attached to a recipient, and an implantable component 104 configured to be implanted under the skin/tissue 101 of the recipient. The cochlear implant system 100 operates with a mobile electronic device 106, which is referred to simply herein as external device 106.

In this example, the implantable component 104 is a cochlear implant and the external component 108 comprises a behind-the-ear (BTE) sound processing unit 110, such as a mini or micro-BTE, and an external coil 112. The sound processing unit 110 comprises one or more sound input elements 111 (e.g., microphones, telecoils, etc.) for receiving sound signals, a power source (not shown in FIG. 1) and a sound processor (also not shown in FIG. 1). The sound processor is configured to process electrical signals generated by the sound input element(s) 111.

The sound processing unit 110 is electrically connected to the external coil 112 via a cable or lead 113. The external coil 112 is an external radio frequency (RF) coil. Generally, a magnet (also not shown in FIG. 1) may be fixed relative to the external coil. Further details of the sound processing unit 110 are provided below with reference to FIG. 3.

FIG. 1 illustrates an example in which the external component 108 includes a BTE and separate external coil 112. However, it is to be appreciated that the external component 108 could alternatively be a component having a generally cylindrical shape that is configured to be magnetically coupled to the recipient's head, sometimes referred to herein as a "button" device, an in-the-canal unit that is configured to be located in the recipient's ear canal, etc.

Figure 2:
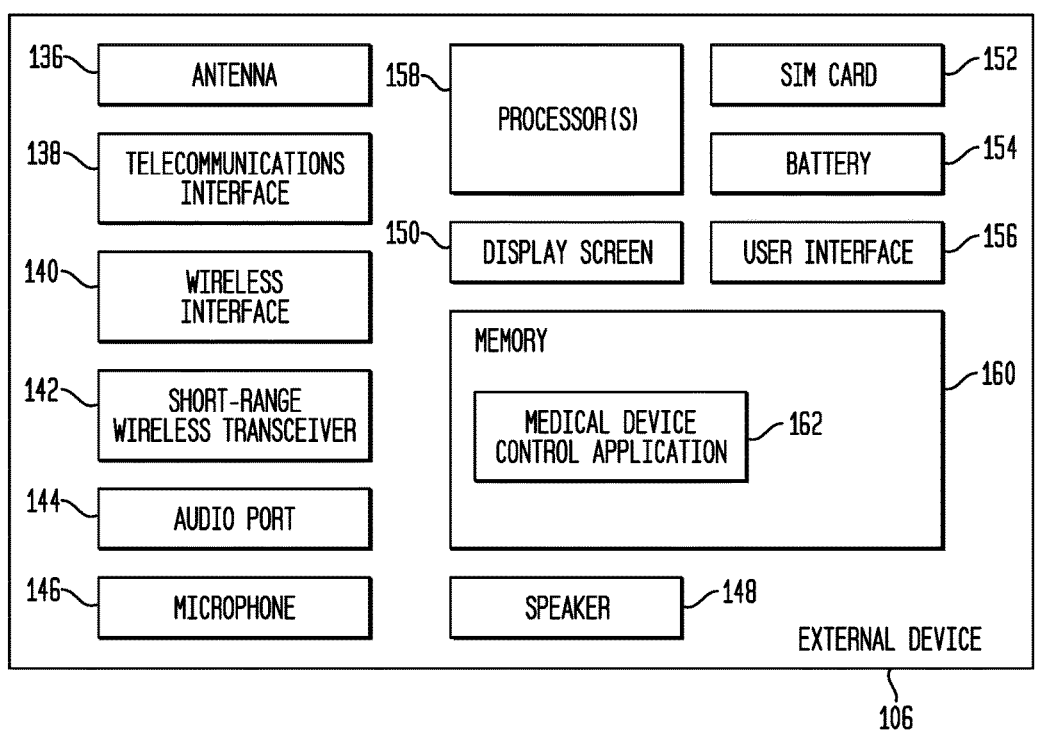
FIG. 2 is a block diagram of an external device operating with a cochlear implant system in accordance with embodiments presented herein.

As noted, the cochlear implant system 100 operates with an external device 106, further details of which are shown in FIG. 2. As described further below, the external device 106 and the sound processing unit 110 each include a short-range wireless transceiver configured for wireless communication in accordance with a short-range wireless standard (i.e., over a short-range wireless link/connection). In certain embodiments, the short-range wireless transceivers are Bluetooth® transceivers that communicate using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. As such, the external device 106 and the sound processing unit 110 communicate over a short-range coupled wireless link/channel 115.

The cochlear implant 104 comprises an implant body 114, a lead region 116, and an elongate intra-cochlear stimulating assembly 118. Elongate stimulating assembly 118 is configured to be at least partially implanted in the cochlea of a recipient and includes a plurality of intra-cochlear stimulating contacts 128. The stimulating contacts 128 collectively form a contact array 126 and may comprise electrical contacts and/or optical contacts. Stimulating assembly 118 extends through an opening in the cochlea (e.g., cochleostomy, the round window, etc.) and has a proximal end connected to the stimulator unit in implant body 114 via lead region 116 that extends through the recipient's mastoid bone.

Cochlear implant 104 also comprises an internal RF coil 120, a magnet fixed relative to the internal coil, a stimulator unit, and a closely coupled wireless transceiver positioned in the implant body 114. The magnets adjacent to external coil 112 and in the cochlear implant 104 facilitate the operational alignment of the external coil 112 with the internal coil 120 in the implant body. The operational alignment of the coils 112 and 120 enables the internal coil 120 to transcutaneously receive power and data from the external coil 112 over the closely-coupled RF link 130. The external and internal coils 112 and 120 are typically wire antenna coils.

FIG. 1 also illustrates a central system 122 that is associated with an outside entity (i.e., an entity other than the recipient), such as the manufacturer of the cochlear implant system 100, a local distributor of the cochlear implant system 100, a clinic or other medical organization, a licensee, etc. However, merely for ease of illustration, the techniques presented herein are described with reference to central system 122 being directly or indirectly controlled (e.g., control contracted to a third party) by the manufacturer of the cochlear implant system 100. In the example of FIG. 1, the central system 122 is a cloud-based software platform (cloud). In the specific illustrative examples presented herein, the cloud-based software platform 122 is sometimes referred to herein as a "manufacturer cloud-based software platform" or simply a "manufacturer cloud." As shown, the manufacturer cloud 122 comprises one or more servers 124 and one or more database systems 132.

As described further below, the external device 106 is a mobile electronic device such as, for example, a remote control device (remote control), a smartphone, etc. The external device 106 has the ability to communicate with the manufacturer cloud 122 via one or more network links (e.g., telecommunications network, wireless local area network, wide area network, etc.) connections 117. It is to be appreciated that the manufacturer cloud 122 would include one or more additional components/devices to enable network connectively of the cloud. Such components are well known in the art and, for ease of illustration, have been omitted from FIG. 1.

FIG. 2 is a block diagram of an arrangement in which the external device 106 is a smartphone. It is to be appreciated that FIG. 2 is merely illustrative and that external device 106 is not limited to the example arrangement shown in FIG. 2.

External device 106 first comprises an antenna 136 and a telecommunications interface 138 that are configured for communication on a telecommunications network. The telecommunications network over which the radio antenna 136 and the radio interface 138 communicate may be, for example, a Global System for Mobile Communications (GSM) network, code division multiple access (CDMA) network, time division multiple access (TDMA), or other kinds of networks.

As shown in FIG. 2, external device 106 also includes a wireless local area network interface 140 and a short-range wireless interface/transceiver 142 (e.g., an infrared (IR) or Bluetooth® transceiver). Bluetooth® is a registered trademark owned by the Bluetooth® SIG. The wireless local area network interface 140 allows the external device 106 to connect to the Internet, while the short-range wireless transceiver 142 enables the external device 106 to wirelessly communicate (i.e., directly receive and transmit data to/from another device via a wireless connection), such as over a 2.4 Gigahertz (GHz) link. As described further below, the short-range wireless transceiver 142 is used to wirelessly connect the external device 106 to sound processing unit 110. It is to be appreciated that that any other interfaces now known or later developed including, but not limited to, Institute of Electrical and Electronics Engineers (IEEE) 802.11, IEEE 802.16 (WiMAX), fixed line, Long Term Evolution (LTE), etc., may also or alternatively form part of the external device 106.

In the example of FIG. 2, external device 106 also comprises an audio port 144, one or more sound input elements, such as a microphone 146, a speaker 148, a display screen 150, a subscriber identity module or subscriber identification module (SIM) card 152, a battery 154, a user interface 156, one or more processors 158, and a memory 160. Stored in memory 160 is medical device control application (logic) 162.

The display screen 150 is an output device, such as a liquid crystal display (LCD), for presentation of visual information to the cochlear implant recipient. The user interface 156 may take many different forms and may include, for example, a keypad, keyboard, mouse, touchscreen, display screen, etc. Memory 160 may comprise any one or more of read only memory (ROM), random access memory (RAM), magnetic disk storage media devices, optical storage media devices, flash memory devices, electrical, optical, or other physical/tangible memory storage devices. The one or more processors 158 are, for example, microprocessors or microcontrollers that execute instructions for the medical device control application 162 stored in memory 160.

Figure 3:
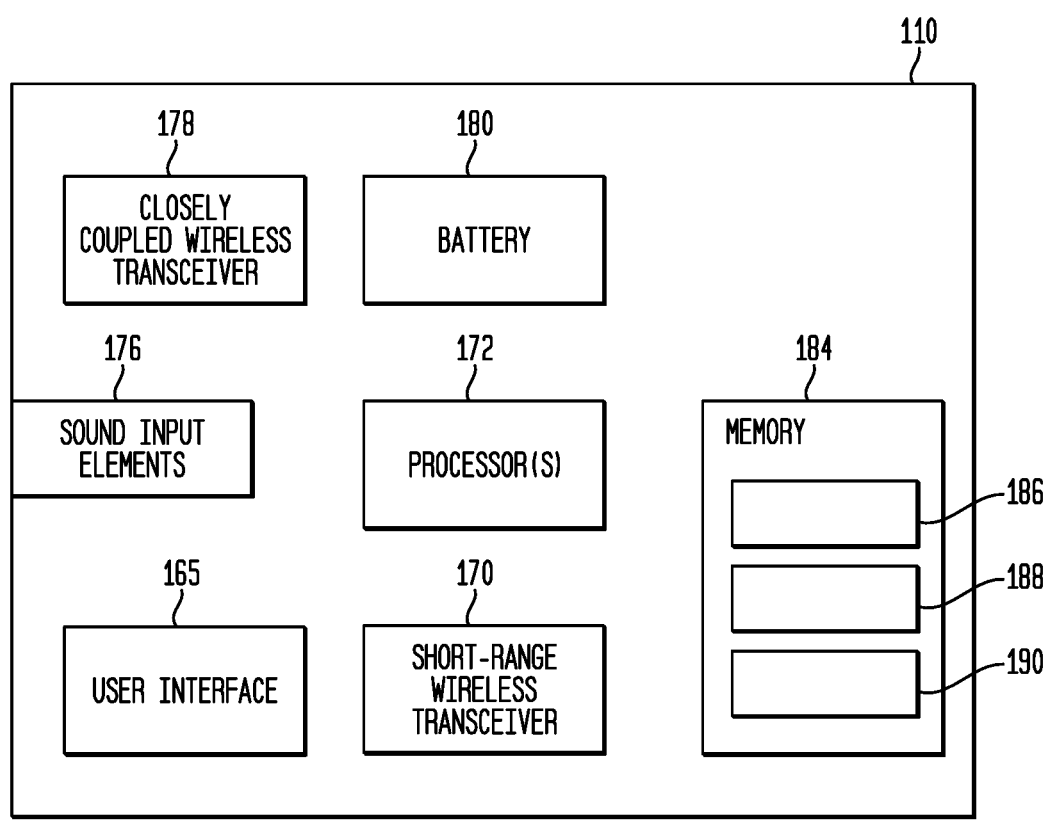
FIG. 3 is a block diagram of a sound processing unit of a cochlear implant system in accordance with embodiments presented herein.

FIG. 3 is a functional block diagram illustrating elements of sound processing unit 110 in accordance with an example embodiment. Shown in FIG. 3 is a short-range wireless transceiver 170, a closely coupled wireless transceiver (i.e., RF encoder/coil driver) 178 that is connected to the RF coil 112 (FIG. 1), a user interface 165 that includes at least one user input device (e.g., push button) and, optionally a display (e.g., numerical display), one or more processors 172, one or more sound input elements 176 (e.g., microphones telecoils, audio input port, Universal Serial Bus (USB) port, etc., and a rechargeable battery 180, such as an integrated or removable lithium-ion (LiIon) battery. Sound processing unit 110 also includes a memory 184 that includes external control logic 186, a serial number 188, and a nonce 190.

The closely coupled wireless transceiver 178 is configured to transcutaneously transmit power and/or data to, and/or receive data from, cochlear implant 104 via the closely coupled RF link 130 (FIG. 1). As used herein, closely coupled wireless communication refers to communications that require close proximity between the communicating transceivers. In one specific example, closely coupled communication refers to communication between transceivers that are within approximately ten (10) centimeters (cm) of one another and/or are inductively coupled to one another. Although FIGS. 1 and 3 illustrate the use of an RF link, it is to be appreciated that alternative embodiments may use other types of closely coupled links (e.g., infrared (IR), capacitive, etc.).

Memory 184 may comprise any one or more of read only memory (ROM), random access memory (RAM), magnetic disk storage media devices, optical storage media devices, flash memory devices, electrical, optical, or other physical/tangible memory storage devices. The one or more processors 172 may be one or more microprocessors or microcontrollers that executes instructions for the external control logic 186 stored in memory 160.

The one or more processors 172 also include a sound processor that is configured to convert sound signals received via the one or more sound input elements 176 into a coded signal that represents stimulation signals for delivery to the recipient and evoke perception of the sound signals. The coded signals generated by the sound processor are transmitted over the closely coupled RF link 130 to cochlear implant 104.

As noted elsewhere herein, the external device 106 is configured to allow a user (e.g., recipient, caregiver, clinician, surgeon, etc.) to control functions of the cochlear implant system 100. This control is enabled, at least in part, via execution of the medical device control application 162 by the one or more processors 158 (FIG. 2) and execution of the external control logic 186 by the one or more processors 172 (FIG. 3). Merely for ease of illustration, embodiments of the present invention are generally described with reference to operations performed by the external device 106 and the sound processing unit 110 without making specific reference to performance of operations by the one or more processors 158, one or more processors 172, the medical device control application 162, and/or the external control logic 186.

Figure 4:
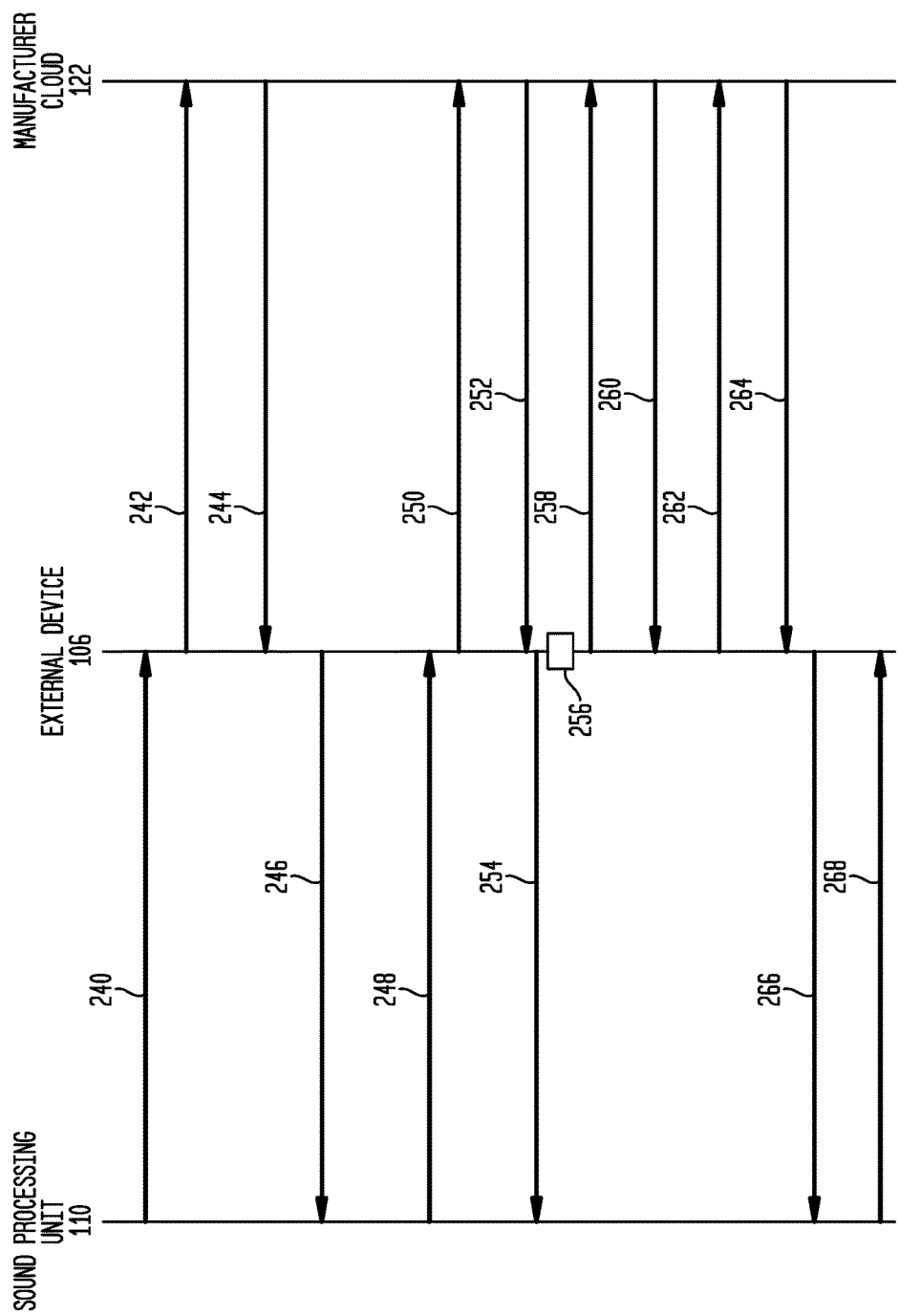
FIG. 4 is a flow diagram illustrating communications in accordance with embodiments presented herein.

FIG. 4 is a flow diagram illustrating communications exchanged between the manufacturer cloud 122 and the external device 106, as well as between the sound processing unit 110 and the external device 106 in accordance with embodiments presented herein. In general, the techniques presented herein address cyber security concerns for cochlear implant system 100 by (1) securing communications between the sound processing unit 110 and manufacturer cloud 122, and (2) ensuring only intended users have access to and are able to control the sound cochlear implant system 100 from an external device.

The techniques presented herein address these two cyber security components via a two-stage (two-phase) process. The first phase (encryption phase) is used to verify the authenticity of the sound processing unit 110 and the manufacturer cloud-based software platform 122 to one another and establish/create an indirect secure channel between the sound processing unit 110 and the manufacturer cloud 122. The indirect secure channel is generally shown in FIG. 1 by bi-directional arrow 119.

The second phase (authorization phase) ensures that only intended users have access to and are able to control the cochlear implant system 100 from external device 106. More specifically, the second phase (1) identifies a user at external device 106, (2) determines whether the identified user should be allowed to control the sound processing unit 110, and (3) determines the level of control that the user should be granted over the cochlear implant system 100. Each of these phases is described further below with reference to FIG. 4.

As noted above, the sound processing unit 110 does not have the ability to connect directly to the manufacturer cloud 122 (i.e., no telecommunications and/or wireless local area network interface interfaces). However, the sound processing unit 110 has the ability to wirelessly communicate with the external device 106 via a short-range wireless link. As such, the techniques presented herein use the external device 106 not unlike an intermediary relay device (e.g., modem) to forward communications between the sound processing unit 110 and the manufacturer cloud 122 and vice versa. Communications between the sound processing unit 110 and the external device 106 are sent over the short-range wireless channel 115, while communications between the external device 106 and the manufacturer cloud 122 are sent over the network connections 117.

The sound processing unit 110 initially has identification information stored therein that is required for the encryption process. This identification information may include, for example, the serial number of the sound processing unit 112 and a series of randomly generated bytes of information/data, sometimes referred to as "nonce data" or simply a "nonce." This nonce initially stored in the sound processing unit 110 is specific to the sound processing unit and, as such, is referred to herein as the "sound processing unit nonce." The serial number, which as noted above is shown in FIG. 3 at reference number 188, and the sound processing unit nonce, which also as noted above shown in FIG. 3 at reference number 190, are stored in an irretrievable manner in the sound processing unit 110 during the manufacturing process.

Referring to FIG. 4 and the first phase for encrypting secure communications sent between the sound processing unit 110 and manufacturer cloud 122, the sound processing unit 110 sends the stored identification information to the external device 106. The sending of the stored identity information to the external device 106 is represented in FIG. 4 by arrow 240. In certain embodiments, the external device 106 is configured to request the identification information from the sound processing unit 110. The request, which has been omitted from FIG. 4 for ease of illustration, may be sent, for example, automatically upon connection to the sound processing unit, in response to user input, in response to a command received from the manufacturer cloud, etc.

The identity information (e.g., serial number and sound processing unit nonce) received at the external device 106 is unusable by the external device 106 and the external device 106 sends the identity information to the manufacturer cloud 122. The sending of the identity information from the external device 106 to the manufacturer cloud 122 is represented in FIG. 4 by arrow 242.

The manufacturer cloud 122 uses the identity information to recognize/identify the specific sound processing unit 110 and uses a pre-existing encryption key to encrypt the received sound processing unit nonce. The pre-existing key that is used to encrypt the received sound processing unit nonce is a pre-determined key that is known to both the manufacturer cloud 122 and the sound processing unit 110 (i.e., a pre-determined encryption key pair stored in the sound processing unit 110 during manufacturing and known/accessible to the manufacturer cloud 122). The manufacturer cloud 122 may obtain the pre-existing encryption key from, for example, one of the database systems 132.

Additionally, the manufacturer cloud 122 generates its own random nonce, which is also encrypted using the pre-existing encryption key. This nonce generated by the manufacturer cloud 122 is specific to the manufacturer cloud 122 and, as such, is referred to herein as the "cloud nonce data" or simple "cloud nonce." As described further below, the randomly generated cloud nonce will be used to generate the "secondary encryption key" that is not reliant on the pre-existing key pair that is known to both the manufacturer cloud 122 and the sound processing unit 110. The encrypted sound processing nonce and the encrypted cloud nonce (each encrypted using the pre-existing encryption key that is known to both the manufacturer cloud 122 and the sound processing unit 110) form a block of encrypted data to generate an encrypted verification message that, as shown by arrow 244, is sent to the external device 106.

The encrypted verification message cannot be interpreted by the external device 106 as it has no familiarity with the encryption scheme in place between the sound processing unit 110 and the manufacturer cloud 122 (i.e., no knowledge of the pre-existing key pair). Therefore, as shown by arrow 246, the external device 106 passes the encrypted verification message to the sound processing unit 110.

Upon receipt of the encrypted verification message, the sound processing unit 110 is configured to execute cryptographic processing to decrypt the encrypted verification message using the same pre-existing key pair described above. This process can take a significant period of time (e.g., 10 to 12 seconds) because the pre-existing key pair is complex (i.e., complex cryptographic algorithms) and because the sound processing unit 110 has limited available power and computation capabilities. That is, the sound processing unit 110 is a battery powered device configured to be worn by a recipient. As such, the sound processing unit 110 has constraints that limit the amount of power and processing capabilities that may be allocated to the cryptographic processing, making the pre-existing encryption key ill suited for low power devices.

If the sound processing unit 110 successfully decrypts the received encrypted verification message, then the sound processing unit determines that it is communicating with the manufacturer cloud 122 (i.e., not being spoofed or intercepted). That is, by decrypting the encrypted verification message, the sound processing unit 110 verifies authenticity of the manufacturer cloud to know that it is communicating with the bona fide manufacturer cloud. As a result, the sound processing unit 110 now has the cloud nonce. The sound processing unit 110 is then configured to use the cloud nonce to randomly generate a new encryption key that is useable for future communications with the manufacturer cloud 122. This randomly generated encryption key, which is is sometimes referred to herein as the secondary encryption key, is a randomly generated chunk of binary data.

The sound processing unit 110 again uses the same pre-existing key pair described above to encrypt the secondary encryption key (i.e., the sound processing unit 110 generates an encrypted payload that includes the secondary encryption key) and, as shown by arrow 248, sends this to the external device 106. Again, since the secondary encryption key is encrypted, the external device 106 cannot interpret the received payload. Therefore, as shown by arrow 250, the external device 106 sends the encrypted payload (secondary encryption key) to the manufacturer cloud 122.

Upon receipt of the encrypted payload, the manufacturer cloud 122 uses the same pre-existing key pair described above to decrypt the secondary encryption key. Receipt of the secondary encryption key causes the manufacturer cloud 122 to determine/verify that the sound processing unit 110 is authentic. As a result, the manufacturer cloud 122 may generate and send a response message to the sound processing unit 110 indicating that the secondary encryption key has been accepted. This response message is represented in FIG.

4 by arrows 252 (i.e., message from manufacturer cloud 122 to external device 106) and arrows 254 (i.e., message from external device 106 to sound processing unit 110).

Acceptance of the secondary encryption key by the manufacturer cloud 122 indicates that the manufacturer cloud has accepted use of the secondary encryption key for encrypting communications sent to the sound processing unit 110. That is, after acceptance of the secondary encryption key, the manufacturer cloud 122 is configured to encrypt all communications directed to sound processing unit 110 using the secondary encryption key, and vice versa. Since the receiving device (either the manufacturer cloud 122 or the sound processing unit 110) has the secondary encryption key, the encrypted communications can be decrypted and recovered.

Communications 240 through 254 illustrate the first (encryption) phase of the techniques presented herein. At the end of the encryption phase, both the sound processing unit 110 and the manufacturer cloud 122 have verified the authenticity of the other party, are able to communicate between each other securely via an intermediary relay device, and the intermediary device is unable to intercept any communication transferred between the sound processing unit 110 and the manufacturer cloud 122.

As noted, the encryption phase ensures that the sound processing unit 110 and the manufacturer cloud 122 can communicate with one another. However, an important piece to this communication is the generation of the secondary encryption key and its use in favor of the pre-existing encryption key (i.e., replacement of the pre-existing encryption key with the secondary encryption key). More specifically, as described above, some initial setup communications between the manufacturer cloud 122 and the sound processing unit 110 are encrypted using the pre-existing encryption key. However, also as described above, this pre-existing encryption key is complex and the associated cryptographic algorithms may take a significant period of time (e.g., 10-12 seconds) to execute at the battery powered sound processing unit 110. Again, this delay is a result of the low power nature of the sound processing unit 110 and the limited processing resources available at the sound processing unit, making the pre-existing encryption key ill suited for low power devices.

Therefore, as described above, in order to avoid a significant delay each time a communication is sent to, or received from, the manufacturer cloud 122, the sound processing unit 110 generates the secondary encryption key, which is less computationally expensive than the pre-existing encryption key. The sound processing unit 110 then sends the secondary encryption key to the manufacturer cloud 122 for subsequent use. However, the secondary encryption key cannot be securely shared between two parties without the use of the pre-existing encryption key. In other words, expensive cryptography is used to establish initial communications. However, once the initial communications are established and the manufacturer cloud 122 and the sound processing unit 110 have verified the authenticity of one another, the manufacturer cloud 122 and the sound processing unit 110 use less expensive cryptography for subsequent communications (i.e., the pre-existing encryption key is initially used to establish and securely share the secondary encryption key).

The concept of replacing the computationally expensive cryptographic key (i.e., the pre-existing encryption key) with a computationally inexpensive cryptographic key (i.e., the secondary encryption key) is a result of the computation abilities and low-power availability of the sound processing unit 110. In communications between devices with ample power and computation abilities, there is no need or desire to switch to a less computationally inexpensive cryptographic key. In fact, such a change runs counter to typical cybersecurity techniques that attempt to use increasingly sophisticated encryption mechanisms to prevent cyber attacks.

Returning specifically to FIG. 4, the second phase of the techniques presented herein relates to authentication of a user at an external device 106 and determining a level of control (if any) that the user can exert over the cochlear implant system 100 from the external device 106. Initially, as shown by box 256 in FIG. 4, the external device 106 (i.e., the medical device control application 162) identifies the user. In one example, a personal identification number (PIN) code is included on a PIN card that is provided to a user with the sound processing unit 110 (e.g., inside the boxed packaging of the sound processing unit). The PIN code is unique for the sound processing unit 110 and is written to the memory 164 (FIG. 3) of the sound processing unit 110 during the manufacturing process. The PIN code is known only to the sound processing unit 110, the manufacturer cloud 122, and the user by virtue of the fact that the user has ownership of the PIN card.

In other examples, user login credentials can be used as an identification mechanism. In such examples, the user will login to a secured user authentication system served up through the manufacturer cloud 122.

At 256, the external device 106 may prompt the user to enter the PIN code via the user interface 156 (FIG. 2). As shown by arrow 258, the external device 106 forwards the PIN code entered by the user to the manufacturer cloud 122. As noted, the manufacturer cloud 122 has knowledge of the PIN code associated with the specific sound processing unit 110 during manufacturing (e.g., the manufacturer cloud 122 is integrated with a manufacturing system database that stores PIN codes for manufactured devices). If the PIN code entered by the user matches the PIN code associated with the specific sound processing unit 110 during manufacturing (i.e., the entered PIN code matches the known PIN from the manufacturing system database), then the manufacturer cloud 122 responds to the external device 106 with a session key that it can use to request access tokens. Sending of the session key to the external device 106 is represented in FIG. 4 by arrow 260.

Upon receipt of the session key, the external device 106 issues a control request to the manufacturer cloud 122. The control request, which is represented in FIG. 4 by arrow 262, requests the ability to control one or more aspects of the sound processing unit 110. The control request includes several pieces of information including the serial number of the sound processing unit 110, a requested/desired level or type of access control, and the session key that was received from the manufacturer cloud 122. The session key operates as an authenticity check to verify that the external device 106 is authorized to make requests for access to the sound processing unit 110.

Upon receipt of the control request 262, the manufacturer cloud 122 evaluates the level/type of control that is requested by the external device 106. The level of control that is requested may take a number of different forms and may be based, for example, on one or more user inputs. For example, different levels of control may be granted to recipients, clinicians, and/or surgeons. The level of control may be determined based on a variety of factors, including inputs received at the external device 106. For example, for elevated levels of access, the user may be required to enter additional information identifying themselves as a clinician or surgeon and this information would be evaluated at the manufacturer cloud 122 (e.g., by comparing entered information to one or more clinician/surgeon databases).

Returning to FIG. 4, if the manufacturer cloud 122 determines that the level of control requested in the control request cannot be granted, the manufacturer cloud is configured to deny the external device 106 access to the sound processing unit 110. In such examples, the manufacturer cloud 122 may also prompt the external device 106 to issue a new control request with a different level of requested access.

If the manufacturer cloud 122 determines that the level of control requested in the control request can be granted, the manufacturer cloud is configured to send the external device 106 a token indicating that the external device has been granted the requested access to the sound processing unit 110. More specifically, the manufacturer cloud 122 will send a message, shown in FIG. 4 by arrow 264, that includes an encrypted access token and an expiration date for the access token. The encrypted access token is encrypted using the secondary encryption key (described above) and, as such, the access token cannot be decrypted by the external device 106. However, the expiration date associated with the access token is unencrypted and allows the external device 106 to know when the token will expire and by when the external device 106 will need to issue another control request to obtain a new access token.

As shown by arrow 266, the external device 106 passes the encrypted access token to the sound processing unit 110. Once decrypted by the sound processing unit 110, the access token provides instructions for the sound processing unit 110 to grant the external device 106 access to one or more functions. The specific level of access to be granted is identified as part of the access token. The sound processing unit 110 is also provided with the expiration date for the access token and the expiration date is stored within the sound processing unit. As such, the access token is forcibly expired by the sound processing unit 110 at the expiration date. In essence, the expiration date informs the sound processing unit that the external device is authorized for a specified period of time with a specified level of functionality.

As shown by arrow 268, after receipt and decryption of the access token, the sound processing unit 110 responds to the external device with a message indicating that the access token has been accepted and that the requested level of functionality has been unlocked to the sound processing unit 110. Therefore, at the end of this authorization phase, the sound processing unit 110 has a secure (encrypted) communication between itself and the manufacturer cloud 122 and has authorized a user to control one or more functions of the sound processing unit via the external device 106.

As noted above, an aspect of the second (authorization) phase is that it relies on the secondary encryption key determined during the first (encryption) phase so that the access control is off-loaded to the manufacturer cloud 122. That is, the manufacturer cloud 122 operates as a proxy for the sound processing unit 110 in regards to authorization control. In this way, the user authorization determination can take advantage of the processing capabilities and information available at the manufacturer cloud 122, rather than relying on only the limited processing and information accessible to the sound processing unit 110.

Embodiments of the present invention have been primarily described above with reference to a cochlear implant system 100 that includes an external sound processing unit 110. It is to be appreciated that embodiments of the present invention may be also implemented in cochlear implant systems, or other implantable medical device systems, that do not include external components. For examples, embodiments of the present invention may be implemented in a totally implantable cochlear implant, where all components of the cochlear implant are configured to be implanted under skin/tissue of the recipient. Because all components of such a cochlear implant are implantable, the cochlear implant is configured to operate, for at least a finite period of time, without the need of an external component. In such examples, above described operations of the sound processing unit 110 would be performed by an implantable component that at least includes one or more processors, a memory, and a wireless transceiver for direct or indirect communication with the external device 106.

FIG. 5 is a flowchart of a method 300 in accordance with embodiments presented herein. Method 300 begins at 302 where an indirect secure communication channel is established, via an intermediary mobile electronic device, between an implantable medical device system and a central system associated with a manufacturer of the implantable medical device system. At 304, the indirect secure communication channel is used to authorize a user to wirelessly control one or more functions of the implantable medical device system via an external device.

In summary, presented herein are techniques that allow control access to implantable medical device systems to be granted on a per-user basis by identifying and authenticating users via a secure channel formed between an implantable medical device system and a central system. The techniques presented herein also allow a device manufacturer to control the level of functionality that a particular user can access on the device.

Embodiments have primarily been described herein with reference to a cochlear implant system and a headpiece device operating as a temporary secure proxy device for authenticated pairing between the external controller and the implantable component. However, as noted above, embodiments of the present invention may be used in other implantable medical device systems that make use of a different external component other than a headpiece device. In such embodiments, the external component is a device that is coupled/attached to the recipient so as to form a closely coupled link with the implantable component, including other partially and totally implantable hearing prostheses such as auditory brainstem stimulators, bone conduction devices, hybrid devices, implantable acoustic devices such as middle ear implants and direct acoustical cochlear stimulators, and/or other implantable medical devices such as implantable pacemakers, defibrillators, functional electrical stimulators, pain relief stimulators, visual prostheses, implantable sensors, and/or other systems having functional implantable components configured to diagnosis, prevent, monitor, treat or manage a disease or injury or symptom thereof, or configured to investigate, replace or modify the anatomy or of a physiological process.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   sending identification information from an implantable medical device system to a central system via an intermediary mobile electronic device, wherein the identity information includes a serial number of a component of the implantable medical device system and implantable medical device system nonce data;
   using, at the central system, the implantable medical device system nonce data to generate an encrypted verification message that includes nonce data specific to the central system;
   sending the encrypted verification message to the implantable medical device system via the intermediary mobile electronic device;
   based on the encrypted verification message, establishing, at implantable medical device system, an indirect secure communication channel between the implantable medical device system and the central system via the intermediary mobile electronic device; and
   using the indirect secure communication channel to authorize a user to wirelessly control one or more functions of the implantable medical device system via the mobile electronic device.

2. The method of claim 1, wherein the intermediary mobile electronic device is unable to decrypt any communication transferred between the implantable medical device system and the central system on the indirect secure communication channel.

3. The method of claim 1, wherein the implantable medical device system communicates with the intermediary mobile electronic device via a short-range wireless communication channel, and wherein the central system communicates with the intermediary mobile electronic device via one or more network links.

4. The method of claim 1, wherein establishing the indirect secure communication channel between the implantable medical device system and the central system comprises:
   using a pre-existing encryption key that is known to both the implantable medical device system and the central system to decrypt the encrypted verification message sent between the implantable medical device system and the central system.

5. The method of claim 1, wherein using the implantable medical device system nonce data to generate an encrypted verification message that includes nonce data specific to the central system comprises:
   encrypting the data implantable medical device system nonce data using the pre-existing encryption key;
   randomly generating the nonce data specific to the central system;
   encrypting the nonce data specific to the central system using the pre-existing encryption key; and
   sending the encrypted data implantable medical device system nonce data and the encrypted cloud nonce data to the implantable medical device system via the intermediary mobile electronic device in the encrypted verification message.

6. The method of claim 1, further comprising:
   at the implantable medical device system, decrypting the nonce data specific to the central system using the pre-existing encryption key;
   generating a secondary encryption key based on the nonce data specific to the central system;
   encrypting the secondary encryption key using the pre-existing encryption key; and
   sending the encrypted secondary encryption key to the central system via the intermediary mobile electronic device.

7. The method of claim 6, further comprising:
   at the central system, decrypting the secondary encryption key using the pre-existing encryption key to extract the secondary encryption key; and
   configuring the central system to use the secondary encryption key for future communications with the implantable medical device system.

8. The method of claim 7, further comprising:
   generating a response message indicating that the secondary encryption key has been accepted for future use by the central system;
   encrypting the response message using the secondary encryption key; and
   sending the encrypted response message to the implantable medical device system via the intermediary mobile electronic device.

9. A system, comprising:
   a central system;
   an intermediary mobile electronic device; and
   an implantable medical device system configured to send identification information to the central system via the intermediary mobile electronic device, wherein the identity information includes a serial number of a component of the implantable medical device system and implantable medical device system nonce data,
   wherein the central system is configured to use the implantable medical device system nonce data to generate an encrypted verification message that includes nonce data specific to the central system, and to send the encrypted verification message to the implantable medical device system via the intermediary mobile electronic device, and
   wherein the implantable medical device system is configured to use the encrypted verification message to establish an indirect secure communication channel with the central system via the intermediary mobile electronic device, and wherein the indirect secure communication channel is useable authorize a user to wirelessly control one or more functions of the implantable medical device system via the mobile electronic device.

10. The system of claim 9, wherein the intermediary mobile electronic device is unable to decrypt any communication transferred between the implantable medical device system and the central system on the indirect secure communication channel.

11. The system of claim 9, wherein the implantable medical device system is configured to communicate with the intermediary mobile electronic device via a short-range wireless communication channel, and wherein the central system is configured to communicate with the intermediary mobile electronic device via one or more network links.

12. The system of claim 9, wherein to establish the indirect secure communication channel between the implantable medical device system and the central system, the implantable medical device system is configured to:
   use a pre-existing encryption key that is known to both the implantable medical device system and the central system to decrypt the encrypted verification message sent between the implantable medical device system and the central system.

13. The system of claim 9, wherein to use the implantable medical device system nonce data to generate the encrypted verification message that includes nonce data specific to the central system, the central system is configured to:
  encrypt the data implantable medical device system nonce data using the pre-existing encryption key;
  randomly generate the nonce data specific to the central system;
  encrypt the nonce data specific to the central system using the pre-existing encryption key; and
  combine the encrypted data implantable medical device system nonce data with the encrypted cloud nonce data to form the encrypted verification message.

14. The system of claim 9, wherein the implantable medical device system is configured to:
  decrypt the nonce data specific to the central system using the pre-existing encryption key;
  generate a secondary encryption key based on the nonce data specific to the central system;
  encrypt the secondary encryption key using the pre-existing encryption key; and
  send the encrypted secondary encryption key to the central system via the intermediary mobile electronic device.

15. The system of claim 14, wherein the central system is configured to:
  decrypt the secondary encryption key using the pre-existing encryption key to extract the secondary encryption key; and
  use the secondary encryption key for future communications with the implantable medical device system.

16. The system of claim 15, wherein the central system is configured to:
  generate a response message indicating that the secondary encryption key has been accepted for future use by the central system;
  encrypt the response message using the secondary encryption key; and
  send the encrypted response message to the implantable medical device system via the intermediary mobile electronic device.

17. An implantable medical device system, comprising:
  a memory;
  a short-range wireless communication transceiver; and
  one or more processors configured to:
    send identification information from an implantable medical device system to a central system via an intermediary mobile electronic device, wherein the identity information includes a serial number of a component of the implantable medical device system and implantable medical device system nonce data;
    receive, via the intermediary mobile electronic device, an encrypted message sent by the central system, wherein the encrypted message is generated by the central system based on the identity information sent by the implantable medical device system;
    use the encrypted message to establish, via the intermediary mobile electronic device, an indirect secure communication channel with the central system; and
    use the indirect secure communication channel to authorize a user to wirelessly control one or more functions of the implantable medical device system via the mobile electronic device.

18. The implantable medical device system of claim 17, wherein to establish the indirect secure communication channel with the central system, the one or more processors are configured to:
  use a pre-existing encryption key that is known to both the implantable medical device system and the central system to decrypt the encrypted message by the central system.

19. The implantable medical device system of claim 18, wherein the encrypted message includes nonce data specific to the central system, and wherein the one or more processors are configured to:
  decrypt the encrypted message to obtain the nonce data specific to the central system using the pre-existing encryption key;
  generate a secondary encryption key based on the nonce data specific to the central system; and
  encrypt the secondary encryption key using the pre-existing encryption key; and
  send the encrypted secondary encryption key to the central system via the intermediary mobile electronic device.

* * * * *